(12) United States Patent
Trachtenberg

(10) Patent No.: US 9,763,737 B2
(45) Date of Patent: Sep. 19, 2017

(54) LASER ABLATION SYSTEM FOR TISSUE ABLATION

(71) Applicant: John Trachtenberg, Toronto (CA)

(72) Inventor: John Trachtenberg, Toronto (CA)

(*) Notice: Subject to any disclaimer, the term of this patent is extended or adjusted under 35 U.S.C. 154(b) by 457 days.

(21) Appl. No.: 14/324,227

(22) Filed: Jul. 6, 2014

(65) Prior Publication Data

US 2016/0000506 A1 Jan. 7, 2016

(51) Int. Cl.
| | |
|---|---|
| A61B 18/18 | (2006.01) |
| A61B 18/22 | (2006.01) |
| A61B 18/00 | (2006.01) |
| A61B 18/20 | (2006.01) |
| A61B 34/30 | (2016.01) |

(52) U.S. Cl.
CPC .............. *A61B 18/22* (2013.01); *A61B 34/30* (2016.02); *A61B 2018/0016* (2013.01); *A61B 2018/00547* (2013.01); *A61B 2018/00577* (2013.01); *A61B 2018/2005* (2013.01); *A61B 2018/208* (2013.01)

(58) Field of Classification Search
CPC .................. A61B 18/20; A61B 18/22; A61B 2018/00517; A61B 2018/00547; A61B 2018/00571; A61B 2018/00577; A61B 2018/002238
USPC ............... 606/4–18; 607/88–92, 96; 128/898
See application file for complete search history.

(56) References Cited

U.S. PATENT DOCUMENTS

| | | | | |
|---|---|---|---|---|
| 5,000,752 | A * | 3/1991 | Hoskin | A61B 18/203 606/15 |
| 6,355,054 | B1 * | 3/2002 | Neuberger | A61B 18/203 604/20 |
| 6,416,531 | B2 * | 7/2002 | Chen | A61N 5/0601 128/898 |
| 7,723,013 | B2 | 5/2010 | Trachtenberg | |
| 7,824,394 | B2 * | 11/2010 | Manstein | A61B 18/1477 606/41 |
| 7,976,571 | B2 * | 7/2011 | Neuberger | A61N 5/0601 607/88 |
| 8,548,562 | B2 | 10/2013 | Trachtenberg | |
| 2006/0095095 | A1 * | 5/2006 | Cao | A61B 18/22 607/88 |
| 2008/0249517 | A1 * | 10/2008 | Svanberg | G02B 6/3809 606/15 |

* cited by examiner

*Primary Examiner* — Ahmed Farah
(74) *Attorney, Agent, or Firm* — Mark A. Litman & Associates, P.A.

(57) ABSTRACT

A system for ablation of tissue has at least a guideplate having a front surface and a rear surface. The guideplate has multiple guideholes distributed over the front surface and passing from the front surface to the rear surface. The at least three longitudinally advancing laser emitters are on elongated supports. The at least three longitudinally advancing laser emitters on elongated supports have a diameters that allow their passage through the guideholes on the guideplate. Each of the three laser emitters has a projection area for emission of laser energy; and the projection areas for each of the three laser emitters overlapping only a portion of the projection areas for at least two others of the three laser emitters when the at least three laser emitters lie within a single geometric plane. Moving the laser emitters while active devascularizes changing volumes of tumor tissue.

17 Claims, 6 Drawing Sheets

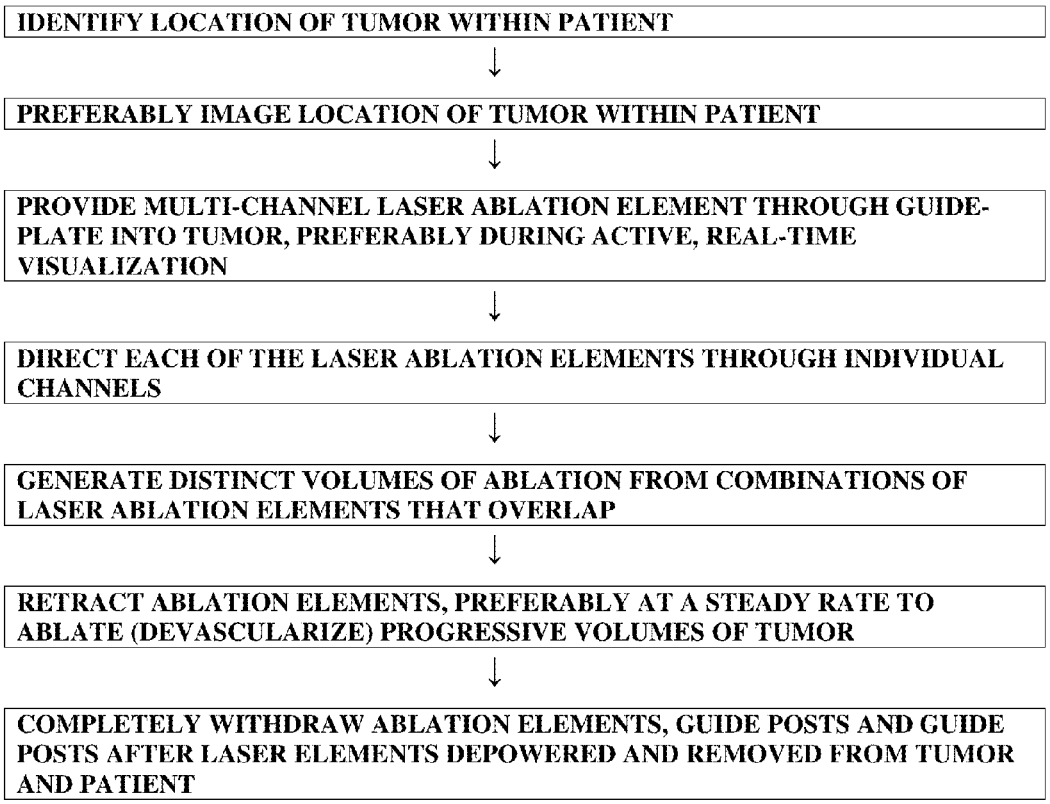

LASER ABLATION SYSTEM FOR TISSUE ABLATION

BACKGROUND OF THE INVENTION

1. Field of the Invention

The invention relates to systems and method of execution of treatments and data accumulation (including imaging data) of those treatments to provide ablation of tissue in a medical procedure. A system and method provides highly effective levels of ablation, especially in malignant tissue target areas so that greater assurance in removal of malignant tissue is afforded during a first procedure. By using imaging techniques and data to differentiate between malignant and non-malignant prostate tissue, tissue removal such as by means of ablation is directed to the malignant tissue, for preservation of the non-malignant tissue in the prostate and surrounding region, thereby minimizing the destructive effects of tissue removal.

2. Background of the Art

Prostate cancer is widely believed to be the most common cancer in men and the second most common cause of death due to cancer. There were approximately 230,000 reported cases of prostate cancer diagnosed in North America in 2005 and over 30,000 deaths. Furthermore, the true prevalence of the disease has been calculated at more than 25% of men over 55. The standard treatments for localized prostate cancer are radical surgery or radiotherapy. These entail ablation of the entire prostate with some degree of unintended collateral damage to surrounding organs. The standard belief is that prostate cancer is a multifocal disease so that treatments are required that target the entire prostate gland. These treatments are neither completely curative nor devoid of side effects. Recent data suggest that this may not be correct in all cases. For the majority of patients low grade and low volume prostate cancer is the prevalent pathological finding and offers minimal risk of morbidity or mortality. Indeed, many believe that radical intervention using standard treatments might offer more harm than good and a strategy of deferred treatment is now being adopted. However, even in this favorable group approximately 20% of men can be expected to die from their disease if followed for long enough.

A new paradigm of therapy is to target selective therapeutic destruction of only the region of malignant (tumor) tissue within the prostate. A histological analysis of over 900 prostatectomy specimens removed for prostate cancer suggest that a solitary dominant lesion is the source of extracapsular in over 80% of patients and thus the likely source of extraprostatic spread. Destruction of this single site is likely to significantly decrease the risk of progression and increase cancer control with minimal side effects. One significant issue in laser ablation is assuring appropriate delivery of energy into the tissue to assure that all malignant tissue within the target area of ablation is removed. Applicant has determined that variations in ablation from single treatments, multiple treatments, single laser ablation elements and even multiple ablation elements have not appropriately provided a system and method that effectively reduces the need for multiple treatments because of the inability to create a uniformly heated and confluent zone of ablation of ablation throughout the target zone, or because of tissue inhomogeneity, needle deflection occurs making accurate target acquisition impossible due to deterioration of image acquisition with each attempted needle pass, or creates too large a window of low energy deposition insufficient for tumor destruction but sufficient to damage adjacent functional tissue such that there is a need for additional treatments. The last issue would create a situation wherein upon later discovery of the insufficiency of malignant tissue removal, more extensive volumes of tissue removal (including adjacent ancillary, non-malignant tissue) to assure a final undesired result.

SUMMARY OF THE INVENTION

The ablation system and attendant method for ablating tissue may be a system for ablation of tissue has 1) a guideplate having a front surface and a rear surface with a distribution of guideholes through the plate. There are 1-5 longitudinally advancing laser emitters on elongated supports. The guideholes may have distributions in spacing and dimensions over the surfaces of the guideplates to accommodate different laser emitting systems and difference dimensions and orientations of the individual emitting elements and supports. The projection areas and/or volumes for each of the 4 laser emitters (in the 4 laser system) overlap only a portion of the projection areas or volumes for at least 3 others of the 4 laser emitters when all laser emitters lie within a single geometric plane perpendicular to the insertion plane. Each of three additional laser emitters placed simultaneously about the initial central placement irrespective of modest deflection obviates multiple needle passes, incurring increased bleeding and decreased imaging accuracy limiting the ultimate ability of MRI thermography to determine uniform and adequate heating. The peripheral laser emissions have the overlapping portion of its projection area overlap from 10-90%, 20-80% or 20-70% of projection areas or projection volumes for each of the at least two others of the laser emitters over the central laser. The system may have each of the at least three peripheral laser emitters advanced simultaneously over the central laser emitter to the proximal edge of the tumor volume, where their individual placement might be independently adjusted of other laser emitters into the single geometric plane or each of the at least three laser emitters are supported by a single stage support element so that the 4 (3 peripheral and 1 central) laser emitters are withdrawn mechanically from the distal placement of the cannula into the prostatic tissue at a variable speed such that a minimum threshold energy density is deposited uniformly along the path of withdrawal, i.e., in areas of supposed high tumor presence the lasers would deposit more energy/cc by being withdrawn slowly and in areas of less tumor the lasers would be withdrawn more quickly to obviate unnecessary tissue damage and speed the procedure. In addition each laser is independently powered to allow "shaping" of the burn, e.g.: to ensure avoidance of adjacent functional tissue a peripheral laser might be depowered all or part of its withdrawal phase, or conversely, if the width of the burn is inadequate all lasers would be illuminate for maximum tissue penetration with adequate energy deposition advance together while they are in the single geometric plane. Finally, since the lasers are withdrawn simultaneously and create a continuous confluent burn along the path of the cannulae there cannot be the apparent undertreated areas when individual laser burns are visually approximated to meet but may not. This device increases precision of the burn, does it faster, and safer.

It is possible to have the laser emitters positioned so that they are not projecting fields within a single plane. This might be intentionally done where the shape or orientation of a tumor or malignant mass suggests such non-uniform planar orientation or emission of the laser energy. For example, where a mass to be treated is sloped at 15 degrees (e.g., leftward) away from an accessible position of entry into the patient, asymmetrical and/or non-planar orientation of the emission fields can assist in appropriate devascularization, especially in conjunction with control of the radii of the emitted fields (e.g., by variation of power input into the individual lasers). This control of angularity, field diameter and the like may be performed by real time observation of the field alone and/or in combination with a software executed plan directing mechanical or manual movement of the sets of lasers and intensity of emissions and the like in the performance of the present technology.

BRIEF DESCRIPTION OF THE DRAWINGS

FIG. 5 shows a schematic of a process according to the present technology.

DETAILED DESCRIPTION OF THE PREFERRED EMBODIMENT

Figure 1:
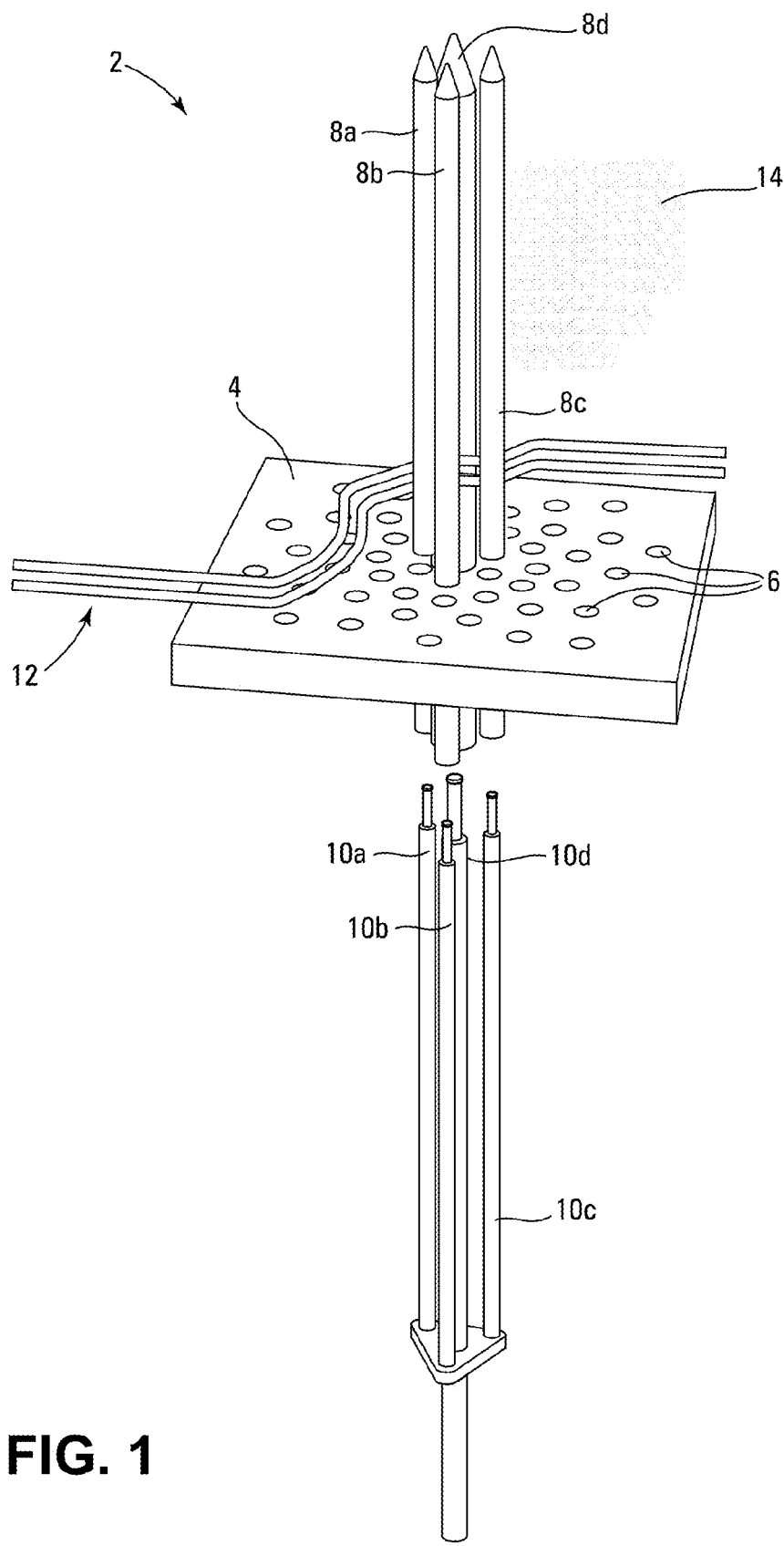
FIG. 1 shows a perspective exploded view of a non-limiting example of a system for performing methods and treatments according to the present invention.

The technology described herein relates generally to apparatus, systems and methods for the treatment of cancer by removal of cancerous (malignant) tissue and cells, while attempting to minimize the removal of or damage to benign (non-cancerous) cells and tissue. The technology described herein is particularly useful for the treatment of prostate cancer where visualization of the tumors, cancerous tissue and differentiation from benign tissue has proven to be difficult by other means. The technology includes, by way of a non-limiting description, at least one ablation system and at least one imaging system (particularly an imaging system that directly provides digital image information or an analog imaging system having a processor that can convert analog imaging data into digital data) that provides data for differentiating between malignant and non-malignant tissues, especially within the prostate region of a patient. The system may also enable guided (automated, robotic, processor plan directed) delivery of tissue removal instrumentation (both for ablative and/or surgical sectioning techniques, by manual or computer-guided formats) to and within the malignant tissues of the prostate, and away from the non-malignant tissues.

The ablation system is a unique system generally described an enabled as follows. A system for ablation of tissue has 1) a guideplate having a front surface and a rear surface. The guideplate should be a structural material with a distribution of guideholes through the plate, from a nominally front surface and a nominally rear surface. The guideplate may comprise metal, polymeric materials, composite materials (combinations of polymers, ceramics, metals, inorganic particles, organic and inorganic fibers and the like). It is not essential that the guideplate be resistant to exposure to the laser energy associated with ablation, although such resistance can be provided. Depending upon the imaging technology, the materials and compositions used in the instrumentality should be varied.

2) There are at least three directionally and especially longitudinally advancing laser emitters on elongated supports. The laser emitters are individually commercially available medical laser ablating elements which project laser energy at sufficient individual fluences (e.g., at least 5,000 Joules/cm$^2$ of ablative energy) for each laser emitter. Such elements can be found as individual commercial components that provide laser energy at fluences sufficient to provide the desired energy levels products and models and manufacturers) and then installed in accordance with the present system. By directionally (as opposed to longitudinally), some of the guideholes may be angled out of perpendicular to the surface of the guideplate so that progression of at least one of the advancing lasers will be non-parallel to the other advancing lasers. Once the dimensions, volumes and orientation of the tumor have been strategically estimated, a plan for positioning the laser path along an effective devascularization path will be implemented by selection of guideholes that allow the individual advancing lasers to progress along lines that will best satisfy the plan. The plan may allow for the nominally central (more centered) laser (which as explained in greater detail may be larger in energy output than other advancing lasers) and at least one additional linearly advancing laser to be mounted on a single support, and other advancing lasers, to accommodate parallel and skewed orientations to the central laser, may be on individual separate supports, on a flexible support attached to the basic support, or at least one laser may be directly advanced (in addition to the laser emitters on the support) without a base support, but just a supporting post.

3) The at least three laser emitters are referred to as directionally (preferably longitudinally) advancing laser emitters as the energy active element are carried on elongated supports. The supports (posts, catheters, cannula, tubes and the like) and the emitting elements have diameters that allow their passage through the guideholes on the guideplate. As will be seen below, the laser emitters (and possibly their advancing supports) may be of different diameters and strength. The holes and available distribution of guideholes in the guideplate should reflect this potential. Although all emitters and supports might be the same dimensions (and the guideholes might then be on uniform diameters), the holes may have distributions in spacing and dimensions over the surfaces of the guideplates to accommodate different laser emitting systems and difference dimensions and orientations of the individual emitting elements and supports.

4) Each of the three laser emitters has a projection area for emission of laser energy. The projection area is usually described as a two-dimensional spot when forward projected at a surface (or surface of a volume) and its energy referenced according to the total amount of energy distributed over that two-dimensional area. Although laser illumination theoretically tends to be uniform, the distribution of energy over the two-dimensional area (often referred to as the 'spot') can vary somewhat because of device inefficiencies (such as deflection of the cannula by a fibrotic or calcified prostate) or tissue inhomogeneity (e.g., calcified areas may actually reflect rather than absorb the laser energy, or areas of intense vascularity in the prostate may increase their auto regulated circulation in response to the heating and serve as an inadvertent but highly effective heat sink, thereby shunting away some or much of the thermal energy deposited and thereby leaving an area of insufficient thermal damage with the potential of prostate tissue (and tumor) survival. The energy emission levels of the individual emitters in ablation treatments may vary, usually over an individual emission intensity of from 1,000-10,000 kJoules/cm$^2$ of ablative energy (or more, although in the practice of the present technology, less, such as 5,000 kJoules/cm$^2$ of ablative energy. As will be shown, a target of total energy fluence from the combined energy of multiple emitters is about 10,000 kJoules/cm$^2$ of ablative energy, so simple mathematics and identification of the amount and number of laser emission overlaps can easily determine desired energy emissions levels. The laser emission may also be calculated in terms of energy emissions per volume (of tissue) into the target area. This is likely a more meaningful perspective. The energy per volume would also be measured in terms of kJoules/cm$^3$ of ablative energy. As there is a time duration involved in the ablation process, 10,000 Joules/cm$^3$ of ablative energy can be delivered over milliseconds by laser emitters each having maximum emission levels and collective maximum emission levels on a surface area determination that is less than 10,000 kJoules/cm$^2$ of ablative energy. The projection areas and/or volumes for each of the three laser emitters overlapping only a portion of the projection areas or volumes for at least two others of the three laser emitters when the at least three laser emitters lie within a single geometric plane. Each of the at least three laser emitters have the overlapping portion of its projection area overlap from 10-90%, 20-80% or 20-70% of projection areas or projection volumes for each of the at least two others of the laser emitters.

5) The system may have each of the at least three laser emitters advance independently of other laser emitters into the single geometric plane or each of the at least three laser emitters are supported by a single stage support element so that the three laser emitters advance together while they are in the single geometric plane.

The system may have at least four longitudinally advancing laser emitters on elongated supports, a central one of the at least four laser emitters being within a triangular space defined by three of the at least four laser emitters, with projection areas and/or projection volumes from each of the at least four laser emitters overlapping at least some are or volume from each of the other at least four laser emitters. The system may have the central one of the laser emitters has a higher laser emission energy potential than each of the three of the at least four laser emitters. Such a system may have projected areas or projected volumes for each of the three of the at least four laser emitters overlap 100% of a projected area for the central one of the at least four laser emitters to provide a fluence of at least 15,000-18,000 J/cm$^3$ (up to 20,000 J/cm$^3$ or more) for the target area or target volume The system may provide projected areas for the three of the at least four laser emitters overlap 100% of a projected area for the central one of the at least four laser emitters so that at least 15,000 J/cm$^3$ is provided at each point within the a projected area for the central one of the at least four laser emitters.

The system may have at least four parallel and longitudinally advancing laser emitters on elongated supports, a central one of the at least four laser emitters being within a triangular space defined by three of the at least four laser emitters and wherein projected areas for the three of the at least four laser emitters overlap 100% of a projected volume for the central one of the at least four laser emitters so that at least 15,000 J/cm$^3$ is provided at each point within the a projected area for the central one of the at least four laser emitters.

The present invention has developed and enabled the concept that to eliminate tumor from the target zone 1) the mpMRI (multiparametric MRI) must be a discrete volume, and highly evidentiary for cancer at stages 4 or 5 in the PIRAD 1-5/5 system (Passive Infrared Detector system). 2) High confluent light energy with a minimum of 15 k J/cc tissue. 3) At the end of the treatment, a Gadolinium enhanced MRI should show marked and uniform devascularization of the entire target zone; if this does not occur, there is a high likelihood of residual tumor in the remaining vascularized zone; however, if residual vascularity is evidenced, the medical practitioner continues to ablate tissue in the specific areas that continue to show vascularization. When it is felt that the area has been satisfactorily ablated, a repeat Gadolinium enhanced scan can be performed to see if that area has been sufficiently devascularized to suggest that any tumor in that zone is no longer viable and thus considered "ablated". In spite of the feeling that such imaging is not possible because of Gadolinium leakage from the damaged vessels, this assumption does not occur to a significant degree and the second and even third scan are easily interpretable.

Thus we have developed the device of the present technology which uses 3-4 lasers being mechanically withdrawn continuously throughout the length of the translucent cannulas to ensure that no area along the light path fails to receive a minimum of 15K J/cc energy. A single fiber will usually suffice for a tumor less than 10 mm in diameter, for wider tumors or tumors with very dense tumor concentrations, the triangular equilateral inserter consisting of 4 obturators is used to insert an additional 3 peripheral parallel cannulas, Each of the peripheral cannulas may be about 1.4 mm OD (e.g., 0.5 to 3.0 mm OD) with the central cannula being larger at 2.4 mm to allow for an initial biopsy of the area under suspicion which can be confirmed immediately by histologic techniques. This high density, tumor-rich, MRI visible tissue could be used, potentially, to develop a systemic personalized anti prostate cancer (or its proliferating factors) vaccine in patients with high grade tumors that harbor, at the time of treatment, unsuspected asymptomatic micro-metastases. If successful, the vaccine would suppress the growth of these tumors so they would not become clinically apparent. The base template that the cannulas are placed through form a circular shape with 10 concentric rings of guideholes each 2.5 mm apart in the radial axis and +30° offset from the guidehole proximal to it as the guideholes extend peripherally. The small inter guidehole gaps (e.g., 1.0 to 4.0 mm, such as about 2.5 mm) and the circular offset nature of the guidehole placement facilitates the correct and rapid insertion of the peripheral cannulas to completely encircle the tumor and to enhance the energy density of the central area approximately 3 fold and double the width of effective cell kill. A second fiber may be placed in the large central cannula to measure light fluence such that were energy deposition so great that tissue became carbonized the decreasing fluence noted would signal a decrease in energy deposited. Similarly, the ability to easily add an additional peripheral cannula containing a fluence measuring fiber at the most lateral or extreme position of a complex shaped tumor would confirm that that zone had been adequately illuminated and likely destroyed. A continuous read out of peripheral fluence above that threshold necessary for irreversible tissue damage would confirm the MRI thermographic maps and spot temperature reading, adding further speed to the thermal work-flow process and decreasing the likelihood of a repeat burn needed because of residual vascularized tissue which presumes residual viable issue and tumor.

This technology may be used in combination with earlier disclosed technology of the inventor (as shown in U.S. Pat. No. 8,548,562) as a system and method to identify the malignant tissue region and a method to focally and selectively destroy the tumor tissue is disclosed for the diagnosis of malignant tissue and prevention of unnecessary damage to non-malignant tissue in the delivery of ablation. The enabled technology is achieved through convergence of technologies that include accurate imaging to detect, localize, and target the malignant tissue within the prostate, an appropriate tissue removal systems such as automated (e.g., robotic) sectioning devices or an ablative device and energy source or any other appropriate surgical device, guided delivery of activity in the automated device or energy from the ablative device, the use of specific software being optional but preferred in treatment planning (e.g., number of lasers necessary and power of each laser at each position in the thermal withdrawal phase to conformally and uniformly deliver adequate energy to completely and uniformly coagulate the target tissue irrespective of its complex shape or size; navigation software designed and validated to place the automated target alignment device at the optimum site of the perineum, calculate the appropriate angle of cannula penetration and the length to thrust the cannula such that it will not damage any intervening tissue and be placed such the initial and if necessary subsequent laser cannula insertions are guided to the optimum position for tumor destruction via near real time MRI scanning of a composite target of both the virtual target obtained in the pretreatment diagnostic multi-parametric MRI and contoured, and registered to the actual treatment 3 dimensional image of the MRI of the prostate and the real time MRI DWI or ADC images seen as the cannula is manipulated to the optimal three dimensional position to achieve complete thermal coverage of the target above the calculated minimum threshold of energy deposited to ablate the tumor in the briefest time possible and using the fewest lasers while sparing adjacent functionally important tissue. In additional, the system will detect in real time the angular degree of deflection of the inserted central cannula in 3 dimensions off the calculated path and if it can be adequately corrected by a corresponding counter angulation to the cannula or increased energy emission, or whether the above described multi laser device should be used. In either case, this system obviates a withdrawal and reinsertion of the central cannula and ensures optimum positioning of the laser(s), In addition, the software then automatically overlays a multi slice (usually 8) representation of the MRI thermography image overlying the anatomic T1w image of the actual pelvis. This allows for an immediate and continuous 3 dimensional rotatable representation of the temperature at any site in the pelvis; heating and automated withdrawal of the laser(s) continues such that a conformal thermal destruction of the tumor target occurs and because of the T1w pelvic overlay representation the adjacent areas containing neurovascular bundles, urethra, rectum can be visualized and avoided minimizing the likelihood of impotence, incontinence, and bowel dysfunction. Gadolinium enhanced MRI immediately following the thermal ablation such that the tumor target is completely devascularized, indicating complete destruction of the target; if a region remains vascularized, the laser(s) are redeployed to the areas still showing active vascularity and laser induced thermal ablation proceeds until no vascularization can be viewed on a subsequent Gd enhanced MRI, suggesting complete destruction of the target (100% MRI thermography of tumor to irreversible tissue damage plus 100% devascularization on Gd enhanced MRI scan suggested elimination of tumor target. The components may be employed sequentially over short or long time span. Advantages of the invention may include at least some of the following: a) improved accuracy in imaging and localization of the tumor (malignant tissues) within the prostate is a result of a novel magnetic resonance imaging-based technique or other contrast-enhancing imaging modalities; b) improved planning for optimizing delivery of therapy to the focal malignant tissue with minimal damage outside the focal volume, based on pre-treatment imaging with or without biopsy; c) improved delivery of ablative therapy to the malignant tissue, such ablative therapy comprising any of thermal therapy (using laser, ultrasound, radiofrequency or microwave energy sources); photodynamic therapy (using a combination of a photosensitizing drug and an activating light source); radiation treatment using either implanted radioactive sources or external ionizing radiation beams; mechanical or other surgical devices to perform a partial prostatectomy; local injection of an anti-cancer agent (drug, biologic, gene, noxious agent); a) improved safety of the system and method through use of minimally-invasively delivery of treatment based on the planning, with or without on-line 3-dimensional sensing and/or imaging of the treatment delivery and tissue response; and b) assessment of the effectiveness of destruction of the target malignant tumor tissue.

In one aspect of the technology described herein, aspects of the present invention provide an imaging system for differentiating between malignant and non-malignant tissues within the prostate region and for guided delivery of specific focal ablation or surgical resection tool to and within the malignant tissues of the prostate, and away from the non-malignant tissues, the system comprising: a) at least one imaging device for receiving image data, processing imaging data and outputting information (which may be in various informative content such as image data or graphic location data, coordinates, perspectives, and the like) bearing on or indicating the size, location, and orientation of the malignant tissue; b) a surgical system (e.g., an energy source and an ablative device for removing tissue such as cutting devices, sectioning devices, ablative devices for deposition of energy into the malignant prostate tissue; and means for quantifying a surgical procedure (such as the energy delivered from the ablative device into the tissue, mass of tissue removed, etc.); wherein the surgical procedure (e.g., ablative energy) is focally delivered by the (e.g.,) ablative device to the malignant tissue under image surveillance so as to substantially avoid destruction of the non-malignant tissue of the prostate.

In another aspect of the technology described herein, the present invention also includes a method of using an ablative device to deliver energy to a malignant prostate region, comprising the steps of: a) differentiating malignant and non-malignant tissues of a prostate, as by identifying the size, location, and orientation of the malignant tissue using an imaging device providing an image display; b) calculating the size, location and orientation of the malignant and non-malignant tissue of the prostate represented on the image display; c) providing an energy source through or from an ablative device to deliver focal ablation to the malignant tissue of the prostate; d) operating a monitoring system arranged to quantify the amount of energy deposited by the ablative device, representative of physiological changes caused by the ablation and to generate output data; and e) delivering focal therapeutic treatment to the malignant tissue of the prostate, in an amount being responsive to the output data of the monitoring system.

According to a further aspect of the technology described herein, the invention includes a method of using a surgical device to resect malignant tissue of a prostate, comprising the steps of: a) differentiating malignant and non-malignant tissues of a prostate, as by identifying the size, location and orientation of the malignant tissue using an imaging device providing an image display; b) calculating the size, location and/or orientation of the malignant and non-malignant tissue of the prostate represented on the image display; and c) providing a surgical device to remove the malignant tissue of the prostate.

According to another aspect of the invention described herein, the invention includes a method of operating a monitoring system to display the remaining prostate tissue during or after surgical removal of the malignant tissue to ensure complete removal of the malignant tissue.

According to another aspect of the invention described herein, the invention includes a computer implemented method for identifying and localizing malignant tissues of a prostate, using T2 weighted imaging, dynamic contrast enhanced imaging, and, diffusion-weighted imaging, comprising the steps of: a) generating a series of axial images through the prostate; b) inputting variable "a" to represent the presence of malignant tissue and variable "b" to represent the absence of malignant tissue in accordance with T2 weighted, diffusion weighted, and dynamic contrast enhanced images, acquired spanning the prostate tissue; c) using a T1 weighted pulse sequence to obtain at least one dynamic contrast enhanced image; d) generating an apparent diffusion coefficient map (ADC) on an MRI scanner using standard software; e) administering an intravenous contrast agent; f) generating a map of parameters from the dynamic contrast enhanced images using a pharmacokinetic model; and g) automatically generating a value reflecting the likelihood of cancer by weighting pre-determined regions of the prostate using a combination of the T2, ADC, and dynamic contrast enhanced parameter maps, This technique may be further enhanced with the use of MR spectroscopy, quantitative T2 mapping or T2* mapping pulse sequences on the MRI system h) Color code and process the image to optimally display the tumor on the background normal prostate to determine the size, location, and orientation of the malignant and non-malignant tissue of the prostate represented on the image display.

According to another aspect of the present technology is enabled a method for ablating tissue within a target area of tissue within a patient in which there are steps of:
a) identifying the target area of tissue where ablation is to be performed;
b) providing a guideplate contiguous to the target area, the guideplate having a front surface and a rear surface, the guideplate having multiple guideholes distributed over the front surface and passing from the front surface to the rear surface;
c) longitudinally advancing at least one laser emitter (preferably multiple laser emitters, more preferably at least three or at least four laser emitters) on an elongated supports through the guideholes on the guideplate towards the target area of tissue;
d) emitting ablative laser energy from the at least one laser emitter so that a projection area from the at least one laser overlaps a first portion of the targeted area within the tissue within the patient; and
e) withdrawing the at least one laser emitter while emitting laser energy to that ablative energy overlaps at least a second portion of the targeted area within the tissue within the patient.

The emitting of laser energy in e) may be done continuously or done intermittently, as with pulses or separately staged emissions after repositioning of the laser emitter(s).

According to another aspect of the invention described here, the invention includes an imaging system for differentiating between malignant and non-malignant tissues within the prostate region and for guided delivery of surgical resection to and within the malignant tissues, the system comprising:
a) at least one imaging device for receiving, processing and outputting the size, location and orientation of the malignant tissue;
b) a surgical device placed into the prostate, either by the operator based on the display of the target malignant tissue in the prostate from the imaging device or by attaching the surgical device to a positioning device capable of receiving data from the imaging device, and
c) translating these data into spatial coordinates that define the position of the surgical device with respect to the position of the target malignant tissue.

A method for ablating or devascularizing tissue within a target area of tissue within a patient may be performed as:
a) identifying the target area of tissue where ablation or devascularization is to be performed;
b) providing a guideplate contiguous to the target area, the guideplate having a front surface and a rear surface, the guideplate having multiple guideholes distributed over the front surface and passing from the front surface to the rear surface;
c) advancing at least three longitudinally advancing laser emitters on elongated supports through the guideholes on the guideplate towards the target area of tissue;
d) contemporaneously emitting ablative laser energy from each of the at least three laser emitters so that projection areas from each of the at least three lasers overlap projection area of at least two others of the at least three laser emitters with 10-90% of projection volumes with energy fluence from each of the at least three laser emitters overlapping each other.

The method may have the at least three laser emitters emitting laser energy while the laser emitters are maintained within a common plane. The at least three laser emitters may be maintained within the common plane while the at least three laser emitters are advancing or retracting so that a volume of tissue is ablated. The method may be practiced where there are at least four longitudinally advancing laser emitters on elongated supports, a central one of the at least four laser emitters being within a triangular space defined by three of the at least four laser emitters and the at least four laser emitters are contemporaneously emitting laser energy. In this last format, the central one of the laser emitters has a higher laser emission energy potential than each of the three of the at least four laser emitters and contemporaneously emits laser energy with the three of the at least four laser emitters at the higher laser emission energy while the three of the at least four laser emitters emit laser energy at energy levels below the higher laser emission level.

The projection areas provide sufficient energy at sufficient flux/area (e.g., 2000 $kJ/cm^2$) to enable sufficient energy/volume to be deposited to devascularize the tumor tissue, which is at least 15000, or preferably at least 18,000 $J/cm^3$ (e.g., up to a reasonable maximum of 20,000) over the dimensions of the tumor. The energy level need not be identical in each projection area, although for simplicity and ease of standardizing the treatments, this is a convenience. The energy/volume is provided to the volume where the three of the at least four laser emitters overlap 100% of a projection area surrounding the at least three laser emitters or a central one of the at least four laser emitters, with three emitters concentrically surrounding a central lumen. The projection areas for the three of the at least four laser emitters overlap 100% of a projection area for the central one of the at least four laser emitters so that at least 15,000 or at least 18,000 J/cm$^3$ is provided at each point within the a projected area (actually a projected volume) for the central one of the at least four laser emitters.

The central hole in the guideplate (and the central support, catheter, lumen, extender passing through the central hole of the four hole guide area) may be bigger (e.g., 25-75% larger, or in this case 50% larger, going from 1.4 mm for the outer holes to 2.6 mm for the center hole) to accommodate additional medical functional apparatus such as a biopsy device which is inserted through the open tip of the central translucent cannula to a) ensure this is an area of high cancer density and b) to collect tissue from this proliferating zone to develop a personalized systemic vaccine. The biopsy device might require about a 2-3 mm diameter (e.g., 2.6 mm) cannula for insertion. When it has accomplished what it needs to do, it is replaced by a 980 nm water cooled laser fiber. All the rest of the holes are smaller because they only will be used to carry a laser fiber (1.4 mm OD of cannula) and 2.5 mm apart (depending upon fiber and guidehole size, from 1.0 to 5 mm apart). The grid pattern is such that an equilateral triangle pattern with arms of 5 mm (e.g., 3 to 8 mm) with the large hole at its center will be completely overlapped by the exemplary 10 mm illuminated diameter of the peripheral lasers. Thus we can double the energy density of the inner portion of the triangle and we can modulate the energy of the lasers via a treatment planning program that mechanically retracts all the lasers simultaneously but varies the power of each laser as well as the speed of withdrawal to ensure a completely coagulated "cylinder with the shape being altered to coagulate maximal tissue where there might be tumor and no structures to be avoided and conversely, with minimal central power and no peripheral power in areas that are desirable to avoid damage. This would all be observed via real time MRI thermography (gives the temperature of tissue with 1° C. precision with a thermography image every 3-4 second overlaying the T1w anatomic image, temperature×time (T×t) calculations give a visible image of irreversibly damaged tissue) and if necessary power of the program being overridden by the operator if not enough or too much tissue were to be damaged. When it appears that entire tumor has been destroyed, a contrast enhanced gadolinium MRI scan is performed and in contrast to the commonly held belief that leakage of the Gd after thermal injury makes interpretation of residual vascularized tissue impossible, in fact, clear images of still vascularized tissue can be easily seen. If this is the case laser heating is resumed and a repeat Gd scan is performed. Our experience suggests that in areas of complete hypo-vascularity on Gd scan after treatment, no tumor persists. The converse is also true; areas of good vascularity will support tumor survival. This is thus a means of confirming adequate thermal damage (treatment).

FIG. 1 shows a perspective exploded view of a system 2 having a guideplate 4 and advancing laser emitter elements 10a, 10b, 10c and 10d according to the present technology. Four guide tubes 8a, 8b, 8c and 8d are inserted through guide holes 6 provided in the guideplate 4. The guide holes 8a, 8b, 8c and 8d are aligned to form a desired distribution of alignment for later inserted advancing laser emitter elements 10a, 10b, 10c and 10d so that a field of overlapped laser emission is formed within a volume to be affected by the laser emissions. The distribution of holes 6 within the guide plate 4 allows for various different orientations, distributions, and numbers of lasers to be inserted during the proposed procedure. The advancing laser emitter elements 10a, 10b, 10c and 10d is matched with the distribution and pattern of the guidetubes 8a, 8b, 8c and 8d. One proposed volume of tumor 14 (here shown on only one side of the guidetubes 8a, 8b, 8c and 8d, while ordinarily they guidetube path would be more centered within a tumor mass because of symmetrical emissions of laser radiation) is shown adjacent the four guide tubes 8a, 8b, 8c and 8d for convenience of illustration. A set of a vein and artery 12 is shown adjacent or against the guideplate 4.

Figure 2:
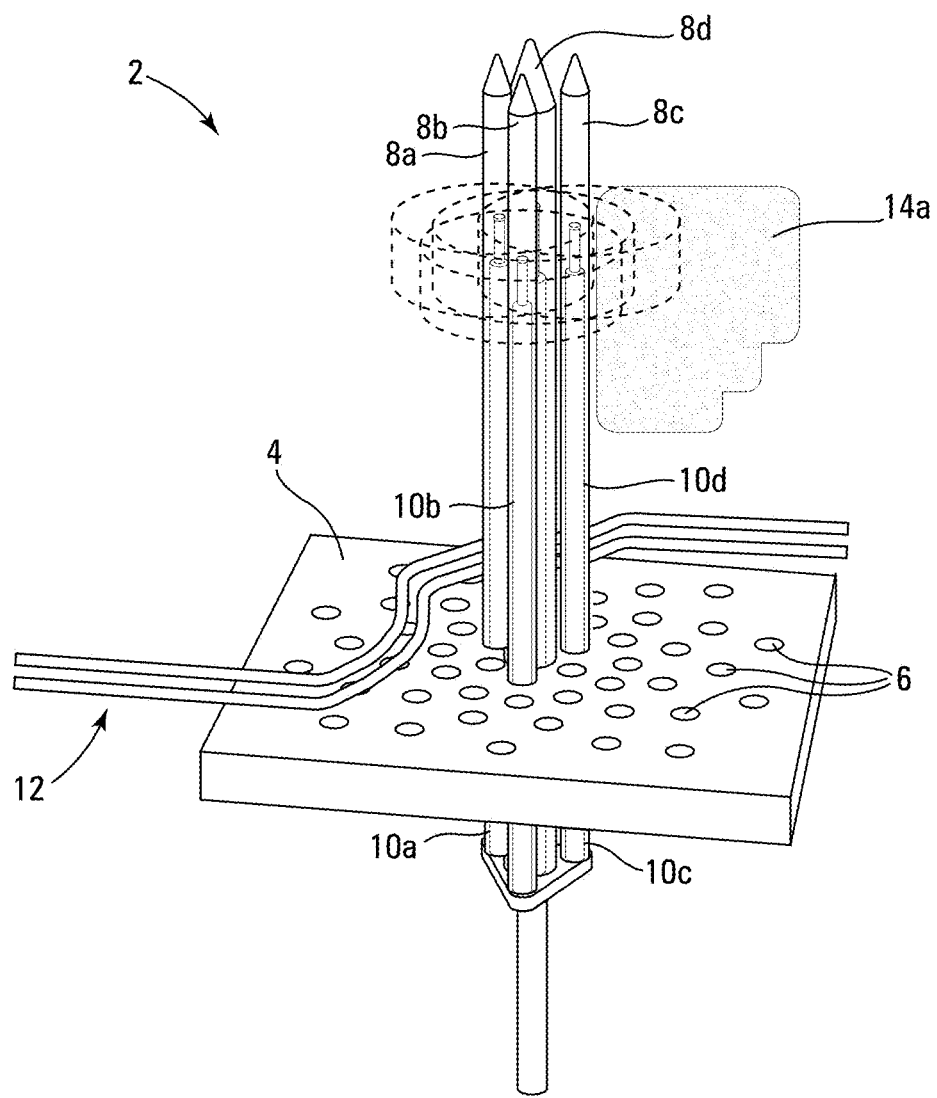
FIG. 2 shows a simplified two-dimensional view of at least a three laser projection spread when the at least three lasers are fired.

FIG. 2 shows a simplified two-dimensional view of at least a three laser projection spread 16 when the at least three lasers 10a, 10b, 10c and 10d are fired within the radiation transparent or translucent guide tubes 8a, 8b, 8c and 8d. Note how the overlapping emission fields 16 extend into the volume of the tumor 14. If the laser emitters 10a, 10b, 10c and 10d are left in place and then turned off, only the tumor mass within the overlapping field 16 would be vascularized. By keeping the laser emitters 10a, 10b, 10c and 10d actively emitting and controllably withdrawing the back through the guide tunes 8a, 8b, 8c and 8d, the overlapping field is drawn over lower volumes of tumor within the tumor mass 14.

Figure 3:
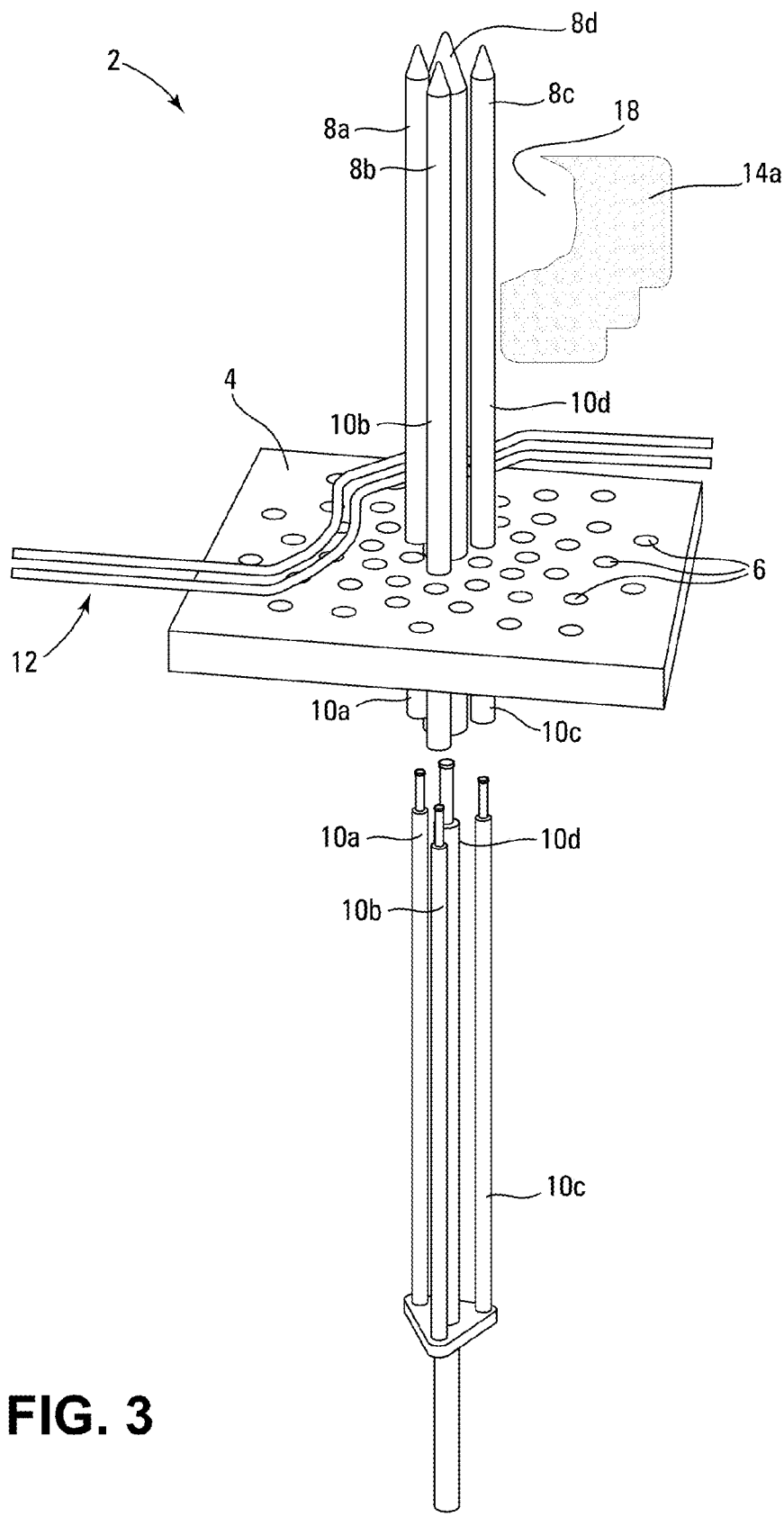
FIG. 3 shows a perspective view after partial withdrawal of the at least three laser emitters to create a partial extended ablation volume.

FIG. 3 shows a perspective view after withdrawal of the at least three laser emitters 10a, 10b, 10c and 10d to create a partial extended ablation volume 18 within the eroded tumor mass 14a. The size of the partial ablated volume 18 can be increased horizontally by any combination of increasing the strength and range of the emitters and repositioning the emitters 10a, 10b, 10c and 10d. The partial ablated volume 18 may be extended vertically or downwardly by moving the emitters 10a, 10b, 10c and 10d while they are energized and emitting radiation at the desired level.

Figure 4A:
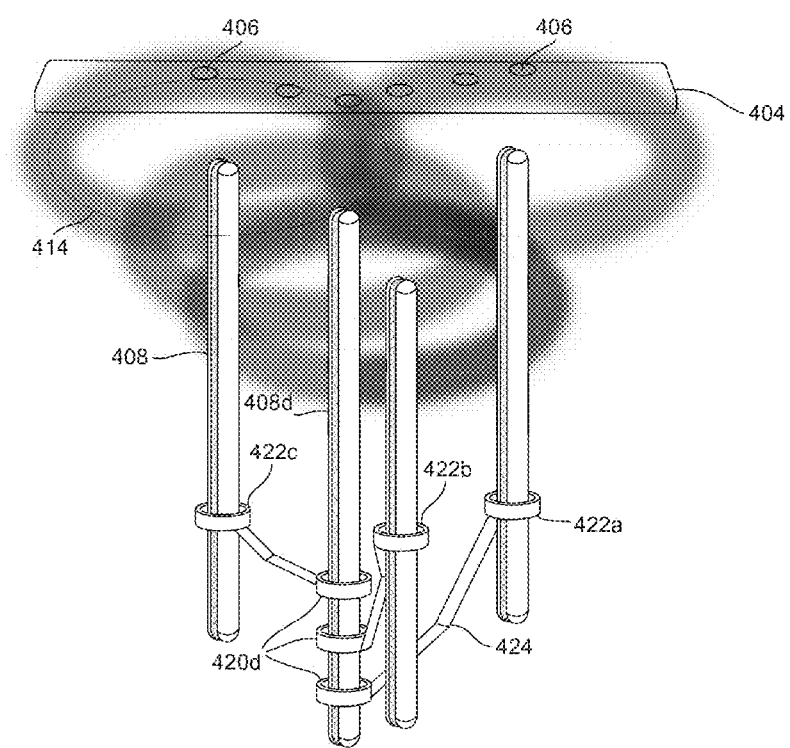
FIG. 4A shows a perspective view of a gimbaled set of adjustable laser projection guides with individual supports for planetary projection guides about the central guide or central post.

FIG. 4A shows a perspective view of an ablative system 400 gimbaled set of adjustable laser projection guides with individual supports 408, 408b, 408c and 408d for planetary projection guides 422a, 422b and 422c about the central guide or central post 420d. Flexible joints 424 are between the individual supports 408, 408b, 408c and 408d for planetary projection guides 422a, 422b and 422c about the central guide or central support 408d. Guide post 408 is secured by gimbaling guide ring 422c which is connected in a flexible manner to central post ring 420d about the central guide post 408b. Each guidepost (after insertion of the central guide post 408b) may be independently directed towards guide holes 406 in guideplate 404. Individual laser fields 414 for each of the laser emitters (not shown) within the individual supports 408, 408b, 408c and 408d are shown. By flexing or gimbaling the position of the planetary projection guides 422a, 422b and 422c about the central guide or central post 420d by flexing the joints 424 the alignment, distribution and angle of the fields 414 may be adjusted. The individual fields may be aligned in parallel or in absolute identical planar alignment, or askew with respect to one or more other fields 414 by appropriate orientation of elements.

Figure 4B:
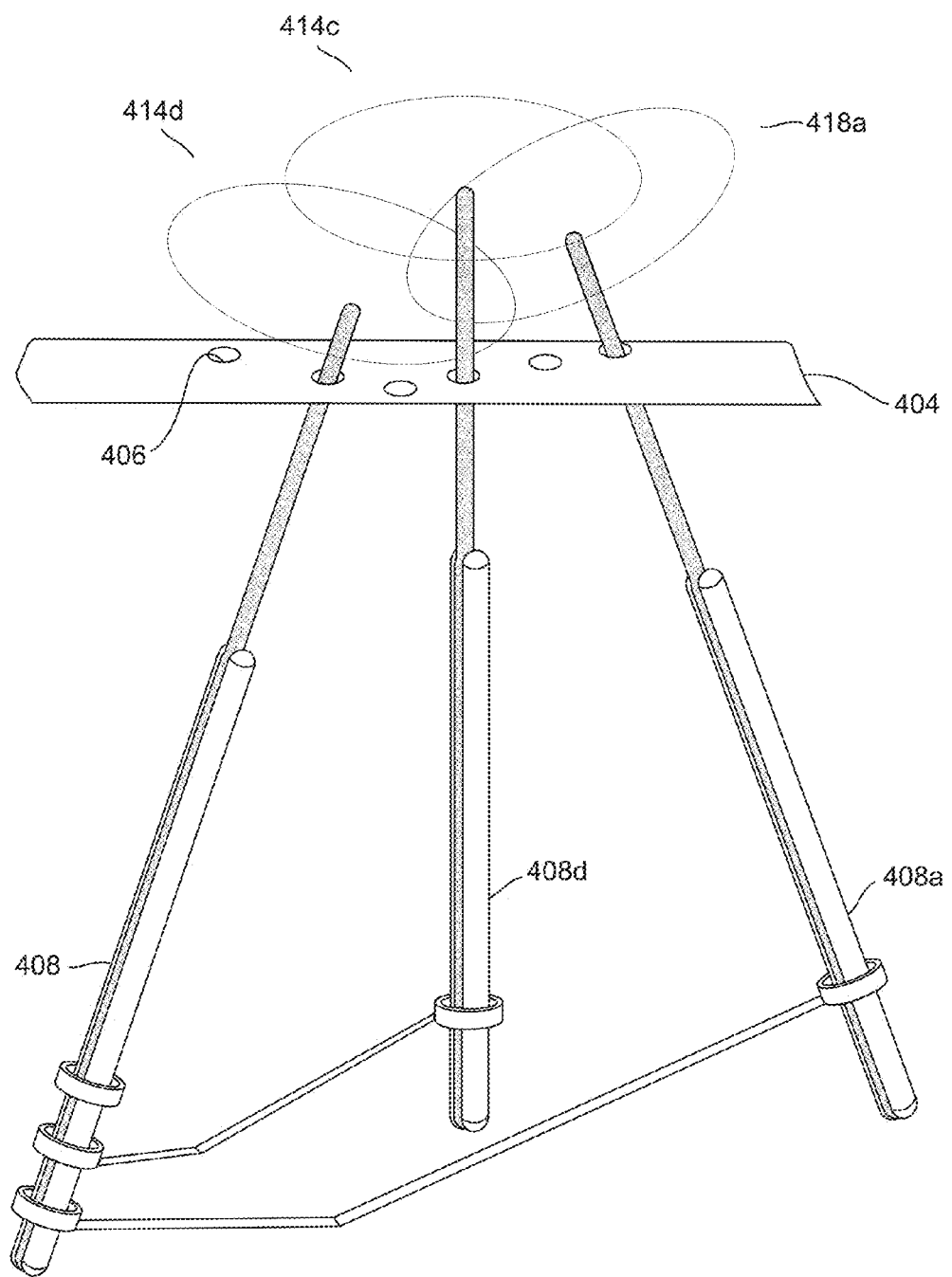
FIG. 4B shows perspective images of coronal and transverse views of the gimbaled set of adjustable laser emitters of FIG. 4B during active emissions creating fields.

FIG. 4B shows a perspective view of the system of FIG. 4A with fields 414a, 414b and 414c created in skewed planes, In the coronal view, a laser emitter 424 extending out of guide post 408a which has passed through guide hole 406 in guideplate 404 is not parallel with other guide posts (e.g., 408bb, 408c, and 408 because of different orientation of the guide post 408a as controlled by the gimbal 422a or by arcuate or angled shaping of the emitter 424 as it leaves the guide post or individual support 408c. With different angularity with respect to each other among individual supports 408, 408a, 408b and 408d, different fields of emission 414c, 418a, (no field shown for 408b evidencing that not all emitters need be turned on) and 414d, respectively. This angularity allows for shaping of the combined fields (e.g., 414a, 414c and 414d) to create angled devascularizing fields rather than only fields within parallel planes. As tumor shapes are not always perfectly geometric, this ability to shape the fields allows for practitioners to match fields with real-life shapes of tumors to maximize devascularization and minimize destruction of healthy tissue. The orientation of the fields may be adjusted during the procedure as required to adjust the field(s) to the changing shape and orientation of the tumor. Real time viewing of the procedure (e.g., MRI, sonogram, fluoroscopy, optical fiber viewing, etc.) can assist in optimizing the work of the practitioner. Therefore materials used in the structure of the guideplates, guide posts, gimbals, flexing elements and emitters should be selected to be compatible with any imaging systems actually used. Such materials may be metals (non-magnetic responsive when used with MRI), composites, polymers, ceramics and the like. Commercially available laser emitters used in the medical field for ablation or devascularization may be used.

The transverse view in FIG. 4B shows the skewed nature of the generated fields 414a, 414b and 414c with no field shown about guide post 408b.

A general description of a useful system may include, again by way of non-limiting examples, a) at least one imaging device for providing imaging data. The system may use analog or digital imaging capture, but ultimate provision as digital data for automated review is preferred. A processor is provided to receive the imaging data and execute software to evaluate the image data according to at least one algorithm. One function that may be provided by the software is to evaluate imaging data according to predetermined standards that are considered in the medical field to be indicative of the appearance of malignant tissue in the region of examination, such as the prostate. The software may be self-executing (e.g., it automatically reads and interprets data, or may pseudo-self-executing with a user inputting partial information to the processor where it is felt that the software should be executed with respect to data in regions and conditions identified by the user input partial information. For example, the processor operator may virtual circle or highlight regions on a view of the imaged field to accentuate regions which to the operators perceptions should be computer evaluated in greatest detail. For example, the imaging information, especially where digitized or initially digital, is provided as columns and rows of imaging data (e.g., pixels or bits in columns and rows of the entire image. By using a touchscreen display of regions of image to the user, regions within the image may be circumscribed, highlighted, detailed, identified or input into the processor as segments of the total image data that can should be particularly screened, analyzed, reviewed, or examined by execution of the software on imaging data within the area of the touchscreen (or other image area selection, as by mouse, coordinate input from an image with an overlaid matrix) identified as of particular interest.

Another variation within the scope of the present technology includes an ablative system including a guidance device constructed so that at least three cannula holders are capable of rotating and/or gimbaling about the central stalk (an insertion post that may or may not carry a laser emitter) of a multi-cannula system. It is the central stalk that slides into an initially placed cannula preferably directing an at least central directional path for a central ablating element. These rotating or gimbaling cannula holders (rotating or gimbaling or flexing about the central stalk, which is preferably fixed in relationship to a guide plate) would resemble a trigonometry compass but would have at least one or two elbow joints (one where the cannula is attached to the device to allow positioning of each of the rotatable cannula to achieve an angle relative to the base plate to be variable (e.g., up to 90 degrees for horizontal alignment/orientation and parallel to the central hole through which passes the central stalk, or a hole with no stalk if it is decided to not to have the cannulas constrained to the horizontal plane). It is desirable to have gimbals at some or each of the base plate holes to allow for a tight fit, yet still allow for angulation. It is also effective to have another or even two simple joints that could be tightened rigidly to hold the cannula. This structure allows each of the ablation energy elements to pass through any (unoccupied) hole in a range of the (for example, 5-10 cm) concentric rings that are about 2.5 cm (±1.5 cm) apart and offset from its previous ring hole by about 30 degrees. Finally, these adjustable cannula holders could be individually attachable to the central spike. This would enable these holders to be able to rotate about the central spike which would be inserted into the cannula placed by the initial pass of the central ablating element (or cannula) towards the target. If the needle is deflected by calcification or firmness of the tumor (e.g., in the prostate) or if the tumor shape is irregular or too wide (>12 mm) additional lasers of any number or shape inserted simultaneously with the second pass such that the overlapping laser fields would conform to the prepared image of the tumor. It is theoretically possible to have an equilateral or obtuse or acute triangle about the central spike if the tumor is essentially linear or have 3 or 4 holders on only one side of the spike in an arc shape such that the burn could, in one pass, create a curve that is confluent to hug the lateral margins of the prostate. All of the laser supports may be able to rotate about the fixed central cannula and obturator and have the capability to angulate if necessary. In case of parallel insertion of the peripheral lasers, lateral elbow joint(s) would be loosened to allow angulation of the laser cannula holder and its obturator. A cable connected to area distal to the joint could be tightened and thus put a medial force above the elbow joint and an equivalent lateral force distal to the joint, thereby applying a lateral force as the rigid cannula-obturator as it passes through the gimbaled guideplate hole where the lateral torque force applied by the cable drives the cannula-obturator distal tip laterally.

Once the ablation radiation translucent cannulas are in the appropriate positions, the obturators could be removed and the laser fibers inserted to the distal tip of each cannula and withdrawn simultaneously at a variable speed, software driven motorized pulley or step motor geared system. The MRI compatible motor could be a step motor or hydraulic piston system to smooth movement during operation of the ablation element. The software would control both the speed of extraction (thereby modulating the energy delivered such that the threshold of about 15000 J/cc is exceeded and could adjust the power of each laser individually to conform closely to the tumor shape or be decreased if adjacent to a structure that must be preserved. An adaptive, conformal, confluent burn may be done in one pass for precision of the zone burned, a burn that traverses the entire zone to be coagulated in one pass ensuring confluence and speed of the burn.

The software may use various analytical techniques that use inclusive, exclusive, edge features, density variations, absolute densities, thermal variations, shape identification and the like to assist in the identification of suspect tissue. The analysis may be on a scholastic basis, assigning relatively subjective values to imaging data that is indicative of a level of probability for tissue to be malignant because of parameters evaluated in the software, percentage estimates for levels of probability, symbolic or color identification of regions according to assessed likelihood of malignancy and the like, as well as absolute standards such as optical density in comparison to a standardized element in an image. This can be done so that an observer may further inspect the regions to provide additional professional input, or to request additional image data from a particular region, as from a different orientation or perspective.

An algorithm may be used for the processing of the imaging data and outputting information relating to size, location and orientation of the malignant tissue and as indicated above, assigning automated estimates of priority for specific regions of the tissue with respect to malignancy or benignity. These assessments may be used to formulate operational procedures and formats, both with regard to the types of instrumentality that may be used in the ultimate surgical treatment and for estimation of the amount of tissue that is to be removed. Based on the probability information provided by analysis of the image data by the software and/or additional user input, plans may be formulated for assumed malignant tissue removal. The medical team, alone or even with patient consultation may decide on the extent of tissue removal (e.g., by physical incision and/or local destruction and/or mass removal, as by ablative, disruptive (sonic disruption, or sectioning) according to plans which may be generally characterized as minimal (e.g., including regions with tissue probabilities for malignancy above 75%); as conservative (e.g., including regions with tissue probabilities at higher levels than in the minimal approach, such as 50%), and radical (e.g., including regions with tissue probabilities at higher levels than in the conservative approach, such as 25%). Different plans may be constructed for suspect tissue removal based on these scholastic or probabilistic assessments of the tissue areas, either from the software alone, or software estimates enhanced by professional input.

The system must use instrumentality to perform the ultimate malignant tissue removal. The instrumentality may be manually operated systems, mechanically (e.g., robotic) operated devices, laser systems distally controlled through a processor or user input, sonic disruption, rf emitter, microwave emitter, chemical application and the like, preferably under visual performance through at least a display device (e.g., monitor or screen). Where there is sonic or laser disruption or destruction of the tissue, there must be an energy source for the operation of the system. A preferred system would be an ablative device for deposition of energy into the malignant prostate tissue.

The energy deposition system must include some control of the deposition of the energy such as a plan and automated or manual control for quantifying the energy delivered from the ablative device into the tissue. A processor is preferably used to provide the plan for the energy to be focally delivered by the ablative device to the malignant tissue under image surveillance so as to substantially avoid destruction of the non-malignant tissue of the prostate based upon the output information relating to size, location and orientation of the malignant tissue. The term focally delivered has the meaning of an identified target region or focus of the intent of the delivery of the operation, and may include, but is clearly not limited to a narrower meaning of focusing energy as through mirrors or lenses. The preferred system has the imaging device comprise an MRI device, although ultrasound, X-ray, fluoroscopy or other non-invasive imaging may be used. Invasive imaging such as fiber optic delivered electromagnetic radiation imaging (e.g., UV, visible or infrared imaging sources), but the non-invasive imaging is highly preferred because of its ease in providing intra-tissue imaging and larger areas of imaging. The other systems would be more likely used to supplement the non-invasive imaging or be used during actual sectioning or ablation of tissue. The system in that event could have the first imaging device as a system providing two distinct imaging capabilities consisting of an MRI device and further comprising at least a second imaging device other than an MRI device. The system or component for quantifying energy deposition from the ablative device may, by way of non-limiting examples, be a plan constructed by application of an algorithm to the imaging data in a computer program. The system may further comprise a minimally invasive monitoring device for monitoring delivery of the energy deposition to the malignant tissue sector, and the minimally invasive monitoring device also verifies non-destruction of the non-malignant tissue sector. The monitoring device may include a screen, display, monitor or the like.

A method of removing malignant tissue from a prostate using ablative energy according to the disclosed technology may be described as comprising at least the steps of taking imaging data by non-invasive imaging; executing a software program using the imaging data to provide an indication of differentiation between malignant and non-malignant tissues of a prostate, determining the size, location and orientation of the malignant and non-malignant tissue of the prostate represented on the image display; providing an energy source through or from an ablative device to deliver focal ablation to the malignant tissue of the prostate in accordance with the determined size, location and orientation of at least the malignant tissue; operating a monitoring system quantifying an amount of energy deposited by the ablative device; and delivering tissue removing focal therapeutic treatment to the malignant tissue of the prostate, in an amount responsive to the output data of the monitoring system. The method may include quantifying the amount of energy as representative of physiological changes to be caused by ablation and the quantified amount of energy generates output data to an ablative device. The obtained determination may preferably indicate size, location and orientation of the malignant tissue by application of an algorithm to the imaging data that characterizes likelihood of grades of data with respect to likelihood of malignancy versus benignity. An imaging device provides an image display during or after the determination. The plan may be prepared as a visual image of proposed location of procedures, a mapping of planned delivery of energy over specific tissue areas within regions identified as containing malignant tissue, by a printed plan in map or coordinate form, or in a database file of plan containing any of the above plan formats.

The technology described herein may also include a method of removing malignant tissue from a prostate using resection by non-ablative tools comprising the steps of: taking imaging data by non-invasive imaging; executing a software program using the imaging data to provide an indication of differentiation between malignant and non-malignant tissues of a prostate, determining the size, location and orientation of the malignant and non-malignant tissue of the prostate represented on the image display; providing a resectioning medical tool to deliver focal therapy of excision of tissue to the malignant tissue of the prostate in accordance with the determined size, location and orientation of at least the malignant tissue; monitoring the amount and location of tissue removed and comparing the tissue removing focal therapeutic treatment to determined size, location and orientation of the malignant tissue. This resectioning method may further comprise operating a monitoring system in real time to display remaining prostate tissue during or after surgical removal of the malignant tissue to ensure complete removal of the malignant tissue.

The technology described herein also encompasses a computer implemented method used in conjunction with the methods described above for energy directed tissue removal methods that includes identifying and localizing malignant tissues of a prostate, using a combination of T2 weighted imaging, dynamic contrast enhanced imaging and diffusion-weighted imaging, comprising the steps of: a) generating a series of axial images through the prostate; b) inputting variable "a" to represent the presence of malignant tissue and variable "b" to represent the absence of malignant tissue in accordance with T2 weighted, diffusion weighted and dynamic contrast enhanced images, acquired spanning the prostate tissue; c) using a T1 weighted pulse sequence to obtain at least one dynamic contrast enhanced image; d) generating an apparent diffusion coefficient map (ADC) on an MRI scanner using standard software; e) administering an intravenous contrast agent; f) generating a permeability map using a modified Brix pharmacokinetic model; and g) automatically generating a value, by weighting pre-determined regions of the permeability map. This is a preferred, but not exclusive method for determining the size, location, and orientation of the malignant and non-malignant tissue of the prostate represented on the image display.

The technology described herein may also include an imaging system for differentiating between malignant and non-malignant tissues within the prostate region and for guided delivery of surgical resection to and within the malignant tissues, the system comprising: a) at least one imaging device for receiving, processing and outputting the size, location and orientation of the malignant tissue; b) a surgical device placed into the prostate, either by the operator based on the display of the target malignant tissue in the prostate from the imaging device or by attaching the surgical device to a positioning device capable of receiving data from the imaging device, and c) translating these data into spatial coordinates that define the position of the surgical device with respect to the position of the target malignant tissue, wherein the surgical device is manipulated under image surveillance so as to remove the malignant tissue while substantially avoiding destruction of the non-malignant tissue of the prostate, the surveillance being provided by a MR, ultrasound or other imaging device that co-registers a) the data from the imaging system used to localize the malignant tissues, b) the position of the surgical device and c) the position and orientation of the prostate during the surgical procedure. In one implementation, malignant cancer within the prostate is localized using a combination of MRI (magnetic resonance imaging) techniques and analysis of the imaging data from the MRI to weight the imaging data with respect to probabilities of tissue or tissue mass providing data indicative of malignancy. These may, for example, comprise the following:

To identify and localize prostate cancer, a format may be used, such as a combination of T2 weighted imaging, dynamic contrast enhanced imaging (DCE) and diffusion weighted imaging is performed: A series of axial images (e.g., full planar slices) is then generated through the prostate. Each region of the prostate is then scored (e.g., evaluated, analyzed to produce a basis of determining likelihood, probability or potential for the presence or absence of cancer. The determination might be based on scholastic ratings or other rankings with a scale available in graphic, look-up table or algorithm that is part of software executed on the processor. In addition to the specific formats and models used in the examples, other known alternative functions and newly developing systems may be used in the practice of this technology, such as but not limited to the use of one or more of T2 mapping, T2* mapping and proton spectroscopy and using other pharmacokinetic models than Modified Brix. The article in Journal of Cerebral Blood Flow and Metabolism, Volume 26, No. 3, "Model selection in magnetic resonance imaging measurements of vascular systems" is incorporated herein by reference for discussion of such modeling systems.

One potential, non-limiting schema for acquiring and scoring the images is outlined below. T2 weighted, diffusion weighted and dynamic contrast enhanced images are acquired spanning the entire prostate volume, normally using a 1.5 T or greater MRI system. T2 weighted images are obtained in two non-parallel planes such as an axial slice and at least one other plane with a slice thickness of 3 mm or less and a field of view of 24 cm or less. In some circumstances an endorectal surface coil may be used to improve spatial resolution with a reduction of field of view to 12-14 cm. Dynamic contrast enhanced images are obtained by using a T1 weighted pulse sequence that allows for repeated imaging of the prostate at a temporal resolution of 100 s or less during the intravenous bolus administration of a low molecular weight MR contrast agent such as a gadolinium chelate (i.e., Gd-DTPA, or gadodiamide). Administration of the intravenous contrast agent may be done using a power injector at a rate of 2-4 ml/s for a total dose of 0.1-0.2 mmol/kg. Specific features used in identifying tumor sites are a relative decrease in T2 signal in the peripheral zone of the prostate combined with elevated permeability. Permeability is derived from a 2 compartment pharmacokinetic model and represents the transfer constant of the contrast agent from the vascular compartment to the tissue compartment.

The present technology may also include operational aspect such as an ability to not only rotate lasers and the plate about a central hole but also to adjust each individual tine (advancing laser). This would allow even more flexibility in addressing a complex shape in a tumor. The plate with the guideholes might resemble something like a trigonometry template for assisting in circle drawing, but with at least three legs that could go at differing distances (e.g., 1.0. 1.25, 2.5, 5, or 7.5 mm etc., from the relatively central laser hole.

In the operation of the system, certain specific procedures ad considerations are made ancillary to the process itself. These may include at least:
1) how and where does a patient get anaesthetized;
2) how the patient is positioned and oriented within an MRI unit;
3) how are robotic controls placed with legs in relatively secure custom stirrups so that there is enough room for movement of an automated alignment device;
4) procedures and protocols to align, check, orient and register mechanics of the laser advancing device;
5) a safety education program, such as a video display comparing what is actually being done versus ideal case, with the possibility of instructions on how to correct deficiencies in real time actual performance of the ablative procedure;

6) each step in the base-line the ideal procedure should be as authentic as possible. Best case actual, simulated or digital graphic arts or animated video clips should illustrate the best case;

7) for simple but practical issues one could show the cannula but carefully illustrate how to use it (e.g., how, where, and what kind of cannula is placed in the central needle holder (present source of cannula) and how it is held in place with obturator;

7) provide a central graphics user interface that will not only show the operator what he is doing but point out the best options, and even identify alternative option and their unique benefits and/or deficiencies;

8) provide a method for auto-contouring of the tumor and automation of perineal alignment with the navigation system recognizing important structures to avoid or we identifying them on a central screen so that path of cannula is as safe as possible yet will get to tumor;

9) in an ideal case of no needle deflection, the supposed width of illumination penetration no more than 10 mm, cannula and obturator 2 to 3 mm past an ADC lesion, a single cooled 30 W fiber is advanced into the distal tip of a cannula, with a non-lethal test fire to ensure accuracy of placement. If evidenced as satisfactory, the tumor should be completely coagulated as viewed by intense red color correlating with temperature of greater than about 60 C with a uniform calculation of greater than 20 KJ/cc tumor with automated software driven fiber withdrawal mechanism so that in areas of high supposed tumor density, withdrawal is relatively slower than in more dense tumor areas, maximizing energy density to get desired treatment plan effect as calculated, ads from pre-Rx 10) the display screen preferably would allow visualization (e.g., auto enhance) adjacent structures that the surgeon would not want to damage, and to keep their colors consistent during operation performance. 11) it would be desirable to have an ancillary system to cool and induce (if necessary) pulses in adjacent vessels. If it turns out that the area to be destroyed is wider than initially presumed, or more complex in shape or the initial needle is deflected too much to be useful (the GUi would automatically give a series of options based on predetermined questions- width of lesion, proximity to NV bundles, presence of visible pulse in NV bundles, proximity to rectum and width of attachment, and tumor at apex etc.)

12) the multi-laser head would be adjusted so that the (preferably at least three additional lasers surrounding the relatively central laser can be adjusted to fit into the circularly drilled template. The central hole may for example be about 2-3 (e.g., 2.6) mm to accommodate an in vivo biopsy device to assure through rapid histology that the target is really the index lesion-sight of increased proliferation and to obtain tissue for personalized systemic vaccine if necessary (probably of value in most Intermediate risk tumors according to recent 18 year review of SPC4.

13) The central stem of the additional head could then be advanced through the central initial cannula bringing an additional 3 lasers with overlapping in-plane fields to markedly increase energy deposition where needed and by rotating. By adjusting the tines of this additional device, the operator could now correct for any deflection of the initial prostate puncture and insert the additional cannula to cover the area missed by the initial puncture without ending up with multiple poor punctures, all deviating in the same direction, which would usually cause bleeding and markedly decreased visibility of the operating field 14) each of the (for example) 4 lasers could be independently controlled such that the burn would correspond to the MRI suggested lesion and not damage adjacent functional tissue.

15) when the thermography suggests that the tumor is fully ablated, a Gd scan with immediate 3D-rendition would be obtained to demonstrate complete devascularization of the tumor volume, if not the particular area that remained vascularized would be retreated until an acceptable Gd scan was obtained.

A specific example of the MRI technology is described below.

MRI Protocol

As a non-limiting example, the following parameters are used to acquire images

1. Equipment

Examinations are performed on a 1.5 T MRI system using an endorectal coil

2. Imaging Planes

Oblique axial imaging is performed perpendicular to the rectoprostatic fascia.

3. Pulse Sequences a. Oblique axial FSE T2 i. Imaging Parameters TR/TE 5650.0/100.4; ETL 16, BW 41.66, FOV 14, PFOV 1.00; slice thickness/gap 3/0 mm, NEX 3, matrix 256.times.256, phase encoding direction left to right, no phase wrap b. Oblique coronal FSE T2 i. same as 3.a.1 but perpendicular plane c. Oblique Axial DWI i. Imaging Parameters TR/TE 4000/73.6 ms, BW 167 kHz; FOV 14.0 cm, PFOV 1.00, slice thickness/gap 3/0 mm; NEX 1; matrix 256.times.128; b-val 600 s/mm 2, phase encoding direction antero-posterior d. Multiphase contrast enhanced 3D FSPGR i. Contrast delivery injection of gadopentetate dimeglumine (MAGNEVIST®, Berlex, N.J., USA) using an automated injector system (Medrad, Pa., USA) at a rate of 4 cc/s and a dose of 0.1 mmol/kg with a 20 cc saline flush at 4 cc/s to commence at the same time as image acquisition. ii. Imaging Parameters Multiphase dynamic T1-weighted 3D gradient echo images will then be obtained over 5 minutes with a temporal resolution of 10 s. TE/TE 6.5/4.2 ms; FA 20; bw 31.25, FOV 14.0 cm; PFOV 1.00; slice thickness 3.0/0.0 mm; NEX 0.5; matrix 256.times.128, phase encoding direction anterior-posterior Abbreviations: TR=repetition time (ms), TE=echo time (ms), BW=bandwidth (kHz); ETL=echo train length, PFOV=phase field of view, FA=flip angle (degrees), NEX=number of excitations, FOV=field of view (cm) FSE=fast spin echo, FSPGR=fast spoiled gradient recalled echo, DWI=diffusion weighted imaging Image Analysis.

Once the image data is acquired they may be analyzed using the following method

T2 Weighted Images

Regions of low signal in the peripheral zone are considered suspicious for cancer. This is a qualitative interpretation.

ADC Maps

From the DWI images (See paragraph c) an apparent diffusion coefficient (ADC) map can be generated on most commercial MRI scanners using standard software.

Permeability Maps

From the dynamic contrast enhanced sequence a permeability map ($k_{trans}$) is generated using a modified Brix pharmacokinetic model as known in the art.

Scoring

Each map may be scored as follows in a given region, by way of non-limiting values as shown is Scholastic Table Set I:

T2 Weighted Images
0—no cancer
1—dark mass like region 1-4 mm
2—dark mass like region >5 mm
3—dark mass like region with high contrast from adjacent areas>5 mm ADC Maps 0—ADC>1000 mm$^2$/s*10$^{-6}$ 3—focal region of ADC<=1000 mm$^2$/s*10$^{-6}$<=3 mm in size 6—focal region of ADC<=1000 mm$^2$/s*10.$^{-6}$>3 mm in size Permeability Maps 0—$k_{trans}$<1 min$^{-1}$ 1—$k_{trans}$>=1 and <10 min$^{-1}$ 2—$k_{trans}$>=10

These scores are then summed for the transition zone and peripheral zone and then interpreted as follows:

Total Score for Peripheral Zone
0 no cancer
1-3 possible cancer
4-5 probable cancer
>5 definite cancer Total Score for Transition Zone
<8 no cancer 8-9 possible cancer
10 definite cancer FIG. 1 in U.S. Pat. No. 8,548,562 Axial Pathologic Section and Corresponding MRI Images Showing Tumor A) Reconstructed pathologic section using older pathologic section method with Gleason 8 tumor outlined by pathologist B) Corresponding area is outline on T2 weighted image (score 2) C) ADC map (scale mm.sup.2/s*10$^{-6}$) from b-value 600 s/mm$^2$ DWI showing dark cancer region (score 6) ADC while permeability and T2 images show mixed changes D) Permeability map from a modified Brix model showing cancer region (white region is >20, Score 2) Total Score is 9=Definite Cancer in the Left Peripheral Zone Other imaging techniques, including but not limited to MR spectroscopy, ultrasound (with or without a contrast-enhancing agent such as microbubbles) or computer-assisted x-ray imaging, may be used as an alternative to or in combination with MR imaging techniques such as that described above or modifications thereof.

Identification of each focal tumor region may be apparent to a person skilled in the art. Optionally, use of computer software for defining the target volume for local therapy in respect of each image is provided to define the size, shape and location of the 3D target region to be treated. Depending on the treatment modality, an algorithm may then be applied to determine the optimal arrangement of, for example, optical fibers, microwave antenna, ultrasound sources such that the focal target (defined in 3D) is destroyed with minimal damage to the normal, non-cancerous regions of the prostate.

The location of the tumor volume(s) within the prostate are translated into a series of Cartesian coordinates relative to bony landmarks of the pelvis and predetermined surface contours of the prostate.

In the case of energy sources for treatment, a treatment planning algorithm and computer program defines, for each source, the dimensions of the source, its location and orientation within or around the target region and the energy or power to be delivered to the target region. The inputs to this algorithm and program include the location of the target malignant tissues as determined by the MR or other imaging device, information on the method of energy delivery and information on the tissue characteristics that determine the distribution of ablative energy or power in the target and non-target tissues in the prostate. These characteristics may be measured in the individual patient prostate or may be, for example, average characteristics measured in other patients.

This treatment plan may then be formulated to define co-ordinates for manual or robotic-assisted surgery for the ablative energy devices. In the case of surgical devices, the location of the malignant tissues may be formulated to define co-ordinates for manual or robotic placement and operation of the surgical devices.

An ablative device, operable according to the optimal parameters as determined by the treatment planning algorithm is provided for treatment delivery. In use, the ablative device is guided for delivery of treatment during the therapeutic procedure. This may be in real time. This may be achieved by using other devices to measure, for example, the energy delivery within and surrounding the focal target region of the prostate in order to adjust the treatment plan to account for variations in the properties of the tissue that affect the distribution of the energy. Alternatively, imaging (dynamic or multiple static images) may be used to monitor the changes to the target tissue (including removal of tissue, coagulation, photoactivation, etc) in response to the treatment. One example is the use of MR imaging on-line in order to map the tissue temperature distribution in the case of thermal destruction or to map changes in tissue vascularity or blood flow. Thereby, a feedback process is implemented. This may either open-loop, in which the operator determines the required changes to the procedure, or closed-loop in which these changes are implemented automatically, for example, under computer control.

In the case or robotic or robotic-assisted treatments, the target coordinates formulated from the output of the treatment planning algorithm and program or formulated directly from the location of the malignant tissue determined by the imaging are translated into directives for the imaging-compatible robot. Thus, for example, this places one or more cannulas into the focal tumor according to the selected treatment plan. The energy-delivery device is then placed in the catheter. Alternatively, the delivery device may be inserted directly without a cannula. Image guidance may be used to assist in the placement of the cannulas or delivery devices and/or to check that these are in the correct position before treatment starts. For surgery-based treatment, the robot or robot-assist provides information on the location of the target tissue to be resected. This may involve the use of stereotactic surgical devices.

This multi-step procedure, comprising targeted, controlled and monitored focal tissue destruction, is continued until the target tumor mass of malignant tissue is eliminated with sparing of the remainder of the prostate gland and of pre-determined adjacent normal (non-malignant) tissues.

In considering a range of alternatives and options within the scope of the practices within the present generic invention, the following values, parameters and techniques will be considered and discussed. Any functionally, laser emitting fiber may be used that can project desired levels of energy are useful. As examples of useful ranges would be 10-75

Watt lasers operating in the near infrared (e.g., 800-1020 nm) such as conventional 15 and 30 W 980 nm laser fibers that carry a geometric (cylindrical) defuser tip or radiation dispersing tip, is (e.g., water) cooled to prevent tissue adjacent to the fiber from charring, Such premature charring would ultimately prevent illumination beyond the charring.

Even using the most sophisticated technology commercially available today (e.g., 3TmpMRI localization and then confirmation of high tumor presence by a mpMRI to a US fusion device (Aremis 2). If that system confirms histologically the hot spot of the so called "Index Lesion," a procedure with that system essentially treats the tissue with what might be considered in the inventor's estimation to be the best system available. Near real time MRI SEQUENCE localization of the confirmed suspicious index lesion or PIRADS 4-5 area of very high suspicion of high density. This would allow for guided and MRI monitored and adaptively controlled focal laser therapy using MRI phase shift thermography in manual, mechatronic and a pure robotic system. That "best" system had a 25% failure rate (in the focal zone), worse than performing the procedure blindly. This type of failure has occurred with other groups that treated very low risk tumors and then attempted to progress through increasing risk prostate tumors found by biopsy after PSA screening or abnormal DRE and confirmed by 1.5 T MRI. The lack of success occurred when each of the tumors were treated by unguided commercial HIFU without follow up with Gd-enhanced MI cans. Even during inventor's own trial of mpMRI to 3-D US fusion FDA pre-approved rigid body fusion device and only occasional delineation of the J &J "Indigo Laser" effect by contrast enhanced ultra sound scanning (I think one of the reasons this study, This technology was the first ever focal study and may have more commercial value than a more reliable and scientifically advanced MRI capability as compared to US (ultrasound) systems today. This may have been relatively weak scientifically, but ultimately had results that approached imaging (but not operational) equivalence to the more rigorous and scientifically alluring MRI mri to mri system that needs some real effort to make it a commercial success. In the operation of the present technology, surgeons were routinely in and out of the OR (operating room) in less than 2 hours). It is not believed that any of the fusion devices really work well because no one has figured out the appropriate way to do the math to allow for real fragmentation analysis and registration of complex movable organs (e.g., the NIH Slicer program, which has been is available as freeware for years but still is regarded as currently sophisticated. Yet it is still not practically usable. The inventor has determined the importance of having overlap in the energy fields of the devascularization energy because one of the main causes of failure was the inability to uniformly overcome the energy density requirements for the treatment to be tumoricidal over a significant and identified volume of the tumor. Furthermore, the technique used was essentially to eyeball the various visible tumor elements from the 3 T and then ADEC real treatment time and then piece by piece destroy the tumor.

It is believed that this previously unstructured way of performing the medical procedure led to the high failure rate. The present system has potential and has been evidenced as being a system where any area considered to be illuminated below the threshold of its destruction by inadequate illumination is identified in the treatment plan pre-operationally. There has to be a better and more reliable method to completely destroy the tumor sites than was previously known, and it is believed that the present technology is an advance. This advance, as described herein, start with improved 'treatment planning'. The present technology provides an improved system with a variety of unique characteristics that overlap.

Benefits of the present technology can include provision of: 1) A modification of a single fired laser tool that can increase energy density per cc of tissue by overlapping several laser emitters in planar lasers; 2) by varying the speed of withdrawal of all of the fibres by a software driven treatment plan that is dependent on the PIRADS risk algorithm, one can increase the energy density per cc of target tissue in areas presumed by the elevated PIRADS to contain a high density of aggressively tumor, by slowing the speed of withdrawal of all of the fibers; and 3) conversely one could decrease the energy delivered in areas felt not to contain tumor (as per mpMRI); 4) by increasing the speed of withdrawal; can illuminate a larger volume at same because of lateral firing lasers; there should not be any gaps in burn because all fibers go down a parallel series of cannula with lasers on and thus are not trying to join multiple burns without actual knowledge of whether margins overlap or are close but where energy delivered is subthreshold (to complete devascularization). This can be accomplished because initial needle placement often deflects because of the inhomogeneity of the prostate. In the present technology. one can simply correct the deflection without the need for multiple needle reinsertions. This is accomplished by using the initial deflected cannula which has already been inserted and is fixed, so that one can slide the Central stem of the triangular (or any shape) peripheral laser holder and in one movement (by compensating for the degree of deflection and insert visually. Of significant importance is that by independently controlling the power of each laser one can CONTROL the burn to conform the exact shape of the mpMRI tumor.

Since various modifications can be made in any invention as herein above described, and many apparently widely different embodiments may be made within the spirit and scope of the claims without departing from the spirit and scope, it is intended that all matter contained in the accompanying specification shall be interpreted as illustrative only and not in a limiting sense.

Working Example on Patient

Mr. CP was a 63-year old man who was diagnosed with prostate cancer on the basis of an elevated PSA (prostate specific antibodies). His clinical stage was T1C and his biopsy showed one core of 6 positive for 15% Gleason grade 6/10 adenocarcinoma. This tumor was in the mid zone of the lateral aspect of the right peripheral portion of the prostate. He sought curative therapy but was discouraged by the known complications of both radical prostatectomy or radiation therapy (both external beam and brachytherapy). He underwent a magnetic resonance scan of the prostate using multi-modal MR scanning (MR map). This was a combination of dynamic contrast enhanced MRI (DCEMRI), and apparent diffusion coefficient images (ADC) generated from diffusion weighted imaging and T2 weighted (T2w) MRI. The scoring scheme described earlier (Scholastic Table Set I) was used to identify a cancer at the right base of the prostate in the peripheral zone. This was traced to generate a 3 dimensional map of the tumor location within the prostate that was stored in memory and displayed on a monitor for professional confirmation. This confirmed the location of the cancer and failed to reveal any other suspicious areas. An energy deposition plan was developed using parameters of tissue density (more dense tissue requiring greater energy levels to ablate), energy levels available from the ablative device, direction of energy delivery by device, available positions or orientations of the ablative device during delivery, location of especially sensitive organs or tissue near regions where ablation is to be performed, format of procedure (conservative, versus, moderate, versus aggressive), and the like, to determine a specific ablation procedure delivery plan. This plan would include considerations of time constraints, available entry positions for the ablative device, available orientations of the ablative device delivery tip with respect to different regions of the tumor, and other physical, mechanical and energy parameters so that even a robotic operation with minimal human control over delivery (except as a fail-safe back-up or refining back-up). He underwent a confirmatory repeat 14-core prostate biopsy which demonstrated no cancer in any other sector of the prostate. Mr. CP consented to magnetic resonance scan directed, ultrasound guided laser focal ablation of the prostate cancer according to procedures and technology described in the present Patent document. A 3-dimensional map of the location of the cancer within the prostate was constructed from the MR map and a plan for the trajectory for placing the ablative photothermal source (830 nm laser) and power setting of the laser were developed using scholastic analysis of the data and assigning scholastic values based solely on mechanically readable Optical Density measurements in the image such that only the sector containing the cancer would be identified and destroyed (avoiding the urethra, rectum, and neurovascular bundles).

Other methodologies that can be used and might be considered in the determination of a plan might include, but are not limited to, an initial area under the enhancement curve (IAUC) or IAUC normalized to a reference tissue being used as a parameter in the determination of the energy/volume that is to be delivered as a property of location throughout the tumor. This energy per volume may vary depending upon the size and orientation of the tumor (malignant tissue) and the tissue density at the malignant tumor regions and the adjacent benign tissue sites. It is also desirable to use both general curve fitting and model based approaches to DCE MRI analysis as a method of either creating a plan or confirming a plan or confirming tissue evaluations for malignancy versus benignity analysis.

The procedure was performed under general anesthetic with the patient in the lithotomy position using transrectal ultrasound guidance and a modified brachytherapy template. A translucent needle was advanced through the template into the prostate under ultrasound guidance following the pre-determined treatment plan such that the laser lay within the substance of the cancer. The obturator of the needle was removed and the laser fiber was advanced into the sheath of the needle. Thermosensors were advanced into the prostate through the template under ultrasound guidance to the edge of the expected ablation zone (1) and another set placed half way between this spot and the vital structure (2) (rectum, urethra). The laser was then power up and temperature was monitored until the zone 1 thermosensors reached 55° C. for 5 minutes while the zone 2 thermosensors stayed below 45° C. At that time the hardware was removed and the patient awakened. The patient was discharged home the following day.

A confirmatory gadolinium enhanced magnetic resonance scan 7 days later showed a devascularized zone coincident to the area of the cancer. No side effects (voiding or erectile) were noted by the patient. A biopsy at 3 months showed no evidence of residual cancer in the prostate.

Other alternative practices within the scope of the present technology include: a method for ablating tissue within a target area of tissue within a patient comprising:

a) identifying the target area of tissue where ablation is to be performed;
b) providing a guideplate contiguous to the target area, the guideplate having a front surface and a rear surface, the guideplate having multiple guideholes distributed over the front surface and passing from the front surface to the rear surface;
c) longitudinally advancing at least one laser emitter on an elongated supports through the guideholes on the guideplate towards the target area of tissue;
d) emitting ablative laser energy from the at least one laser emitter so that a projection area from the at least one laser overlaps a first portion of the targeted area within the tissue within the patient; and
e) withdrawing the at least one laser emitter while emitting laser energy to that ablative energy overlaps at least a second portion of the targeted area within the tissue within the patient, wherein the emitting of laser energy in e) is done intermittently.

The above described system may have the at least one of the at least three longitudinally advancing laser emitters is carried on an elongated support which may be controllably and angularly oriented away from parallel with respect to at least one other of the at least three elongated supports; and the projection areas for at least one of the three laser emitters overlapping only a portion of the projection areas for at least one other of the three laser emitters and the projection areas of at least two of the at least three laser emitters lie within geometric planes that are askew. This system may have at least two or all three of the at least three elongated supports controllably and angularly oriented away from parallel with respect to at least one other of the at least three elongated supports.

The above described general method may also have contemporaneously emitting ablative laser energy from each of the at least three laser emitters, projection areas from at least two of the at least three lasers overlap from askew planes of emitted laser energy.

One non-limiting embodiment illustrating the procedures is presented in FIG. 2. The system may be constructed so that the minimally invasive monitoring device is operable for receiving and processing data from a computer hardware and software device. The present invention is defined by the claims appended hereto, with the foregoing description being merely illustrative of a preferred embodiment of the invention. Those of ordinary skill may envisage certain modifications to the foregoing embodiments which, although not explicitly discussed herein, do not depart from the scope of the invention, as defined by the appended claims.

The present technology may be used for safe, salvage of local recurrences of post radiation prostate cancer that is MRI visible, especially useful where confined to the prostate, and has a psa<10 ng/ml). Although 1/3 men are treated with radiation therapy on diagnosis, few are routinely biopsied post treatment and in those that are, even with a stable PSA of <2 ng/ml, historical trials have shown a recurrence rate of greater than 90%. Little of present medical technology is considered curative, especially if performed on men with PSA>10 ng/ml, and even remains extremely toxic even in experienced practitioners hands with side effect rates that are uniformly high and which confer a severe impact on the patient's Quality of Life (e.g. salvage prostatectomy: urethral stricture 40-70%; recto-vesical fistulae, 4-40%; impotence. >90%; incontinence 50-90%; and if PSA is >4 ng/ml usually recur pretty quickly. In addition, focal MRI guided radiation to high local doses using brachytherapy has been tried but results have been generally poor because there is little basis in evidence as to whether the procedure has succeeded until several months or years later when it is too late (there is no marker of local effectiveness like thermography or Gd scanning showing immediate destruction of the tumor volume when radiation is used. It also can be toxic (fistulae between rectum and bladder or urethra, urethral strictures, anal strictures, rectal cancers, etc.) even when used focally because tissue has already been radiated to its maximum tolerance and has little reserve, or there has been tissue damage or is unable to heal. Many people just cover their technical failures in both radiation and surgery by giving salvage or adjunctive hormone therapy (castration, medical or surgical) which lowers PSA for a while and but is never curative and is toxic itself (induces a so called "metabolic syndrome," akin to having diabetes with 20+ pound weight gain in first year, glucose handling problems, and early death due to cardiac arrhythmias.

Any intra-organ tumor that is visualizable by MRI could be better off when vascularization is done precisely and with less likely injury to adjacent tissue by the technique described herein as "Focal Precision MRI Guided Conformal Coagulation of Any MRI Visible Tumor," These intra-organ tumors may include hepatomas and metastases to the liver that are usually done by RFA blindly looking for only changes in impedance (a lot of collateral damage but inexpensive, same for RFA of small kidney tumors where the lack of visualization and monitored destruction is the cause of numerous bowel and major vessel injuries, (also breast, thyroid etc.).

It is also desirable to include-post-imaging techniques such as morphologic based filters and principal component analysis to assist in plan formation. Morphologic filtering and algorithms for applying such filters and rules are taught, by way of non-limiting examples in U.S. Pat. Nos. 5,491, 627; 5,588,435; and 6,504,959 (these and all other cited references are incorporated in their entireties herein by reference. Also, it is possible to use known gray-tone morphologic rules directly on the unbinarized image, and one could expand the concept of the pixel "neighborhood" to include non-adjacent pixels, with parameters chosen so as not to thicken "noisy" boundaries too much. These and other graphic analytical techniques can be used to establish scholastic values in determining tumor size, orientation and location from image data taken by non-invasive imaging techniques.

What is claimed:

1. A system for ablation of tissue comprising:
a guideplate having a front surface and a rear surface;
the guideplate having multiple guideholes distributed over the front surface and passing through the front surface and through the rear surface;
at least three translucent or transparent guide tubes passing entirely through the guideholes;
at least three longitudinally advancing laser emitters on elongated supports, the at least three longitudinally advancing laser emitters adjustably advancing through the at least three guide tubes;
the at least three longitudinally advancing laser emitters being supported on elongated supports, and the at least three longitudinally advancing laser emitters each having a diameter that allows their passage through the at least three guide posts and through the at least three guideholes on the guideplate;
each of the at least three laser emitters having a projection area for emission of laser energy; and
the projection areas for each of the at least three laser emitters overlapping only a portion of the projection areas for at least two others of the at least three laser emitters when the at least three laser emitters lie within a single geometric plane.

2. The system of claim 1 wherein each of the at least three laser emitters have the overlapping portion of its projection area overlap from 10-90% of projection areas for each of the at least two others of the laser emitters.

3. The system of claim 2 wherein each of the at least three laser emitters can advance independently of other laser emitters into the single geometric plane.

4. The system of claim 2 wherein each of the at least three laser emitters are supported by a single stage support element so that the three laser emitters advance together while they are in the single geometric plane.

5. The system of claim 1 wherein each of the at least three laser emitters have the overlapping portion of its projection area overlap from 20-70% of projection areas for each of the at least two others of the laser emitters.

6. The system of claim 5 wherein each of the at least three laser emitters can advance independently of other laser emitters into the single geometric plane.

7. The system of claim 5 wherein each of the at least three laser emitters are supported by a single stage support element so that the three laser emitters advance together while they are in the single geometric plane.

8. The system of claim 1 wherein the at least one of the at least three longitudinally advancing laser emitters is carried on an elongated support which may be controllably and angularly oriented away from parallel with respect to at least one other of the at least three elongated supports and the projection areas for at least one of the three laser emitters overlapping only a portion of the projection areas for at least one other of the three laser emitters and the projection areas of at least two of the at least three laser emitters lie within geometric planes that are askew.

9. The system of claim 8 wherein at least two of the at least three elongated supports may be controllably and angularly oriented away from parallel with respect to at least one other of the at least three elongated supports.

10. A system for ablation of tissue comprising:
a guideplate having a front surface and a rear surface;
the guideplate having multiple guideholes distributed over the front surface and passing from the front surface to the rear surface;
at least three longitudinally advancing laser emitters on elongated supports;
the at least three longitudinally advancing laser emitters on elongated supports having a diameters that allow their passage through the guideholes on the guideplate;
each of the three laser emitters having a projection area for emission of laser energy; and
the projection areas for each of the three laser emitters overlapping only a portion of the projection areas for at least two others of the three laser emitters when the at least three laser emitters lie within a single geometric planewherein there are at least four longitudinally advancing laser emitters on elongated supports, a central one of the at least four laser emitters being within a triangular space defined by three of the at least four laser emitters.

11. The system of claim 10 wherein the central one of the laser emitters has a higher laser emission energy potential than each of the three of the at least four laser emitters.

12. The system of claim 10 wherein projected volumes of laser emitted energy of at least 15,000J/cm$^3$ is provided for the volume of overlap of three laser emitters overlap.

13. The system of claim 10 wherein projected areas for the three of the at least four laser emitters overlap 100% of a projected volume for the central one of the at least four laser emitters so that at least 15,000J/cm$^3$ is provided at each point within the a projected area for the central one of the at least four laser emitters.

14. A system for ablation of tissue comprising:
a guideplate having a front surface and a rear surface;
the guideplate having multiple guideholes distributed over the front surface and passing from the front surface to the rear surface;
at least three longitudinally advancing laser emitters on elongated supports;
the at least three longitudinally advancing laser emitters on elongated supports having a diameters that allow their passage through the guideholes on the guideplate;
each of the three laser emitters having a projection area for emission of laser energy; and
the projection areas for each of the three laser emitters overlapping only a portion of the projection areas for at least two others of the three laser emitters when the at least three laser emitters lie within a single geometric plane,
wherein each of the at least three laser emitters have the overlapping portion of its projection area overlap from 20-70% of projection areas for each of the at least two others of the laser emitters; and
wherein there are at least four longitudinally advancing laser emitters on elongated supports, a central one of the at least four laser emitters being within a triangular space defined by three of the at least four laser emitters and wherein projected areas for the three of the at least four laser emitters overlap 100% of a projected area for the central one of the at least four laser emitters so that at least 10,000kJ/cm2 is provided at each point within the a projected area for the central one of the at least four laser emitters.

15. The system of claim 14 wherein each of the at least three laser emitters are supported by a single stage support element so that the three laser emitters advance together while they are in the single geometric plane.

16. A system for ablation of tissue comprising:
a guideplate having a front surface and a rear surface;
the guideplate having multiple guideholes distributed over the front surface and passing from the front surface to the rear surface;
at least three longitudinally advancing laser emitters on elongated supports;
the at least three longitudinally advancing laser emitters on elongated supports having a diameters that allow their passage through the guideholes on the guideplate;
each of the three laser emitters having a projection area for emission of laser energy; and
the projection areas for each of the three laser emitters overlapping only a portion of the projection areas for at least two others of the three laser emitters when the at least three laser emitters lie within a single geometric plane;
wherein the at least one of the at least three longitudinally advancing laser emitters is carried on an elongated support which may be controllably and angularly oriented away from parallel with respect to at least one other of the at least three elongated supports and the projection areas for at least one of the three laser emitters overlapping only a portion of the projection areas for at least one other of the three laser emitters and the projection areas of at least two of the at least three laser emitters lie within geometric planes that are askew; and
wherein the elongated support may be controllably and angularly oriented away from parallel by mechanically applying a centrally directed force to a region above a distal elbow joint forcing the distal portion of the guidepost and a proximal portion of the guidepost having passed through a guidehole in the guideplate and is forced laterally off the parallel.

17. The system of claim 16 wherein control and angular orientation of the elongated support is configured for remote control and direction the directed force enables movement of the guidepost off the parallel in at least one of a superior, inferior or lateral direction.

* * * * *